(12) United States Patent
Zhang et al.

(10) Patent No.: US 11,607,663 B2
(45) Date of Patent: Mar. 21, 2023

(54) STRENGTHENING OXIDATION SYSTEM OF EXTERNAL MICRO-INTERFACIAL UNIT FOR PRODUCING PTA WITH PX

(71) Applicant: NANJING YANCHANG REACTION TECHNOLOGY RESEARCH INSTITUTE CO., LTD., Nanjing (CN)

(72) Inventors: Zhibing Zhang, Nanjing (CN); Zheng Zhou, Nanjing (CN); Feng Zhang, Nanjing (CN); Lei Li, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN)

(73) Assignee: NANJING YANCHANG REACTION TECHNOLOGY RESEARCH INSTITUTE CO., LTD., Nanjing (CN)

(*) Notice: Subject to any disclaimer, the term of this patent is extended or adjusted under 35 U.S.C. 154(b) by 0 days.

(21) Appl. No.: 17/778,400

(22) PCT Filed: May 28, 2020

(86) PCT No.: PCT/CN2020/092763
§ 371 (c)(1),
(2) Date: May 19, 2022

(87) PCT Pub. No.: WO2021/196385
PCT Pub. Date: Oct. 7, 2021

(65) Prior Publication Data
US 2022/0395803 A1    Dec. 15, 2022

(30) Foreign Application Priority Data
Mar. 31, 2020    (CN) .......................... 202010243430.1

(51) Int. Cl.
*B01J 10/00*    (2006.01)
*B01J 19/00*    (2006.01)
(Continued)

(52) U.S. Cl.
CPC ........... *B01J 19/244* (2013.01); *B01J 10/002* (2013.01); *B01J 19/0013* (2013.01); *C07C 51/16* (2013.01); *B01J 2219/00081* (2013.01)

(58) Field of Classification Search
CPC . B01J 10/00; B01J 10/002; B01J 19/00; B01J 19/0006; B01J 19/0013; B01J 19/24;
(Continued)

(56) References Cited

U.S. PATENT DOCUMENTS 5,277,878 A * 1/1994 Piotrowski .......... B01F 23/2368
261/153
2013/0036622 A1* 2/2013 Abraham .................. B01J 8/26
34/368

FOREIGN PATENT DOCUMENTS

CN    106179135 A       12/2016
CN    107346378 A    *  11/2017    ............. G16C 20/10
(Continued)

OTHER PUBLICATIONS

Zhang et al. (CN 107346378 A), published on Nov. 14, 2017, with machine translation. (Year: 2017).*

*Primary Examiner* — Natasha E Young

(57) ABSTRACT

A strengthening oxidation system of the external micro-interfacial unit for producing PTA with PX is provided, including: a reactor, a circulating heat exchange device and a micro-interfacial unit. The reactor includes an outer casing and an inner cylinder disposed concentrically inside the outer casing. The circulating heat exchange device is disposed at an exterior of the reactor, and is connected with the outer casing and the inner cylinder respectively, for regulating reaction temperatures of the first reaction zone, the (Continued)

second reaction zone and the third reaction zone inside the reactor in a reaction process of producing PTA with PX. the micro-interfacial unit is connected between the reactor and the circulating heat exchange device, and connected with an external feed pipe of the reactor, for crushing a gas phase material into micro bubbles with a diameter greater than or equal to 1 μm and less than 1 mm and for mixing the micro bubbles with a liquid phase material to form an emulsion at the exterior of the reactor before a reaction material enters each of the reaction zones inside the reactor.

7 Claims, 1 Drawing Sheet

(51) Int. Cl.
*B01J 19/24* (2006.01)
*C07C 51/16* (2006.01)

(58) Field of Classification Search
CPC .. B01J 19/2415; B01J 19/244; B01J 2219/00; B01J 2219/00049; B01J 2219/00051; B01J 2219/00074; B01J 2219/00076; B01J 2219/00081; C07C 51/00; C07C 51/16
See application file for complete search history.

(56) References Cited

FOREIGN PATENT DOCUMENTS

| | | |
|---|---|---|
| CN | 110038491 A | 7/2019 |
| CN | 210079476 U | 2/2020 |

* cited by examiner

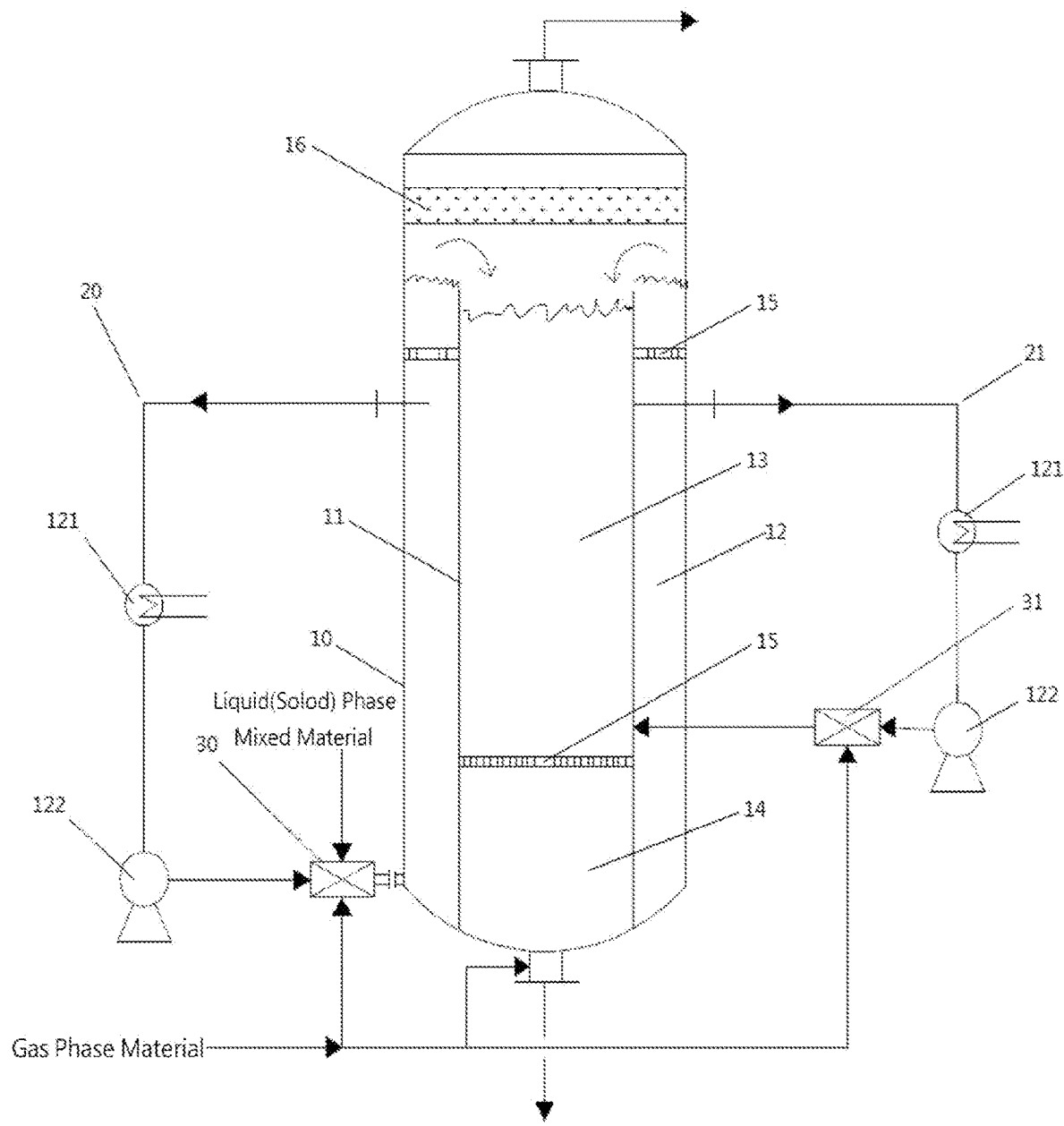

STRENGTHENING OXIDATION SYSTEM OF EXTERNAL MICRO-INTERFACIAL UNIT FOR PRODUCING PTA WITH PX

This application is a national stage application claiming priority to PCT/CN2020/092763, now WO/2021/196385, filed on May 28, 2020, which claims priority to Chinese Patent Application Serial No. CN202010243430.1, filed on Mar. 31, 2020.

FIELD OF THE INVENTION

The present invention relates to the technical field of chemical industry, in particular to a strengthening oxidation system of an external micro-interfacial unit for producing PTA with PX.

BACKGROUND OF THE INVENTION

The oxidation reaction process of producing TA (p-phthalic acid) PX (p-xylene) is very complicated, mainly including 4 steps, i.e., from PX to p-tolualdehyde (TALD) to p-tolualdehyde (p-TA) to 4-carboxy benzaldehyde (4-CBA) to p-phthalic acid (TA). The four oxidation reactions in this reaction process are series reactions, which generally use acetic acid as a solvent, and use cobalt acetate, manganese acetate and hydrobromic acid (or tetrabromomethane) as a catalyst.

Recently, in the existing PTA production technology, the four main steps in the oxidation reaction process are all carried out in the same reactor. Although the reaction rate constants of the above four steps are different by more than ten times, the mixed reaction process is adopted, and different conditions are not given for different reactions, so that the reaction solvent acetic acid is wasted in large quantities under high temperature and high pressure, and the product TA cannot be taken out in time simultaneously, thereby resulting in high energy consumption, large consumption of acetic acid and low reaction efficiency.

SUMMARY OF THE INVENTION

In view of this, the present invention proposes a strengthening oxidation system of an external micro-interfacial unit for producing PTA with PX, aiming at solving the problem that the reaction solvent acetic acid is wasted in high temperature and high pressure during the existing PTA production with PX, and the product TX cannot be taken out in time simultaneously.

The present invention proposes a strengthening oxidation system of an external micro-interfacial unit for producing PTA with PX, including:

a reactor, a circulating heat exchange device and a micro-interfacial unit;

wherein the reactor comprises an outer casing and an inner cylinder disposed concentrically inside the outer casing, the inner cylinder has a bottom end being closed and connected to an inner bottom surface of the outer casing and a top end extending to a top surface of the reactor, a zone between an interior of the outer casing and an exterior of the inner cylinder is a first reaction zone, and an interior of the inner cylinder forms sequentially a second reaction zone and a third reaction zone from top to bottom;

the circulating heat exchange device is disposed at an exterior of the reactor, and is connected with the outer casing and the inner cylinder respectively, for regulating reaction temperatures of the first reaction zone, the second reaction zone and the third reaction zone inside the reactor in a reaction process of producing PTA with PX; and the micro-interfacial unit is connected between the reactor and the circulating heat exchange device, and connected with an external feed pipe of the reactor, for crushing a gas phase material into micro bubbles with a diameter greater than or equal to 1 µm and less than 1 mm and for mixing the micro bubbles with a liquid phase material to form an emulsion at the exterior of the reactor before a reaction material enters each of the reaction zones inside the reactor.

Further, the circulating heat exchange device comprises a first circulating heat exchange pipeline and a second circulating heat exchange pipeline; and wherein:

the first circulating heat exchange pipeline has an inlet end connected to an upper end of a side wall of the outer casing and an outlet end connected with a material inlet of a bottom end of the side wall of the outer casing through the micro-interfacial unit, for regulating the reaction temperature of the first reaction zone; and the second circulating heat exchange pipeline has an inlet end connected to an upper end of a side wall of the inner cylinder and an outlet end connected with a material inlet of a bottom end of the side wall of the inner cylinder through the micro-interfacial unit, for regulating the reaction temperature of the second reaction zone and the reaction temperature of the third reaction zone inside the inner cylinder in the reaction process.

Further, the micro-interfacial unit comprises a first micro-interfacial generator and a second micro-interfacial generator; and wherein:

the first micro-interfacial generator is disposed between the first circulating heat exchange pipeline and the side wall of the outer casing, and is connected with a liquid phase feed pipe and a gas phase feed pipe in the external feed pipe, for crushing an air into the micro bubbles and forming the emulsion with the liquid phase material before the gas phase material enters the first reaction zone; and the second micro-interfacial generator is disposed between the second circulating heat exchange pipeline and the side wall of the inner cylinder, and is connected with the gas phase feed pipe, for crushing the air of the gas phase material into the micro bubbles and forming the emulsion with the liquid phase material before the gas phase material air enters the second reaction zone.

Further, the first reaction zone is a reaction zone where p-xylene is converted into p-tolualdehyde and p-tolualdehyde is converted into p-toluic acid, the second reaction zone is a reaction zone where the p-toluic acid is converted into 4-carboxy benzaldehyde, and the third reaction zone is a reaction zone where the 4-carboxy benzaldehyde is converted into p-phthalic acid.

Further, in the strengthening oxidation system of the external micro-interfacial unit for producing PTA with PX, a bottom of the reactor is provided with a gas phase inlet and a discharge port; and wherein:

the gas phase inlet is connected with the external gas phase feed pipe for providing the air of the gas phase material required for the reaction of the third reaction zone;

the discharge port is used to take out a mixed material containing a reaction product, p-phthalic acid, in the third reaction zone.

Further, in the strengthening oxidation system of the external micro-interfacial unit for producing PTA with PX, a height of the inner cylinder is ⅘ of a height of the outer casing.

Further, in the strengthening oxidation system of the external micro-interfacial unit for producing PTA with PX, a volume of the first reaction zone accounts for 45% of a total reaction volume in the reactor.

Further, in the strengthening oxidation system of the external micro-interfacial unit for producing PTA with PX, a volume of the second reaction zone accounts for 53.5% of the total reaction volume in the reactor.

Further, in the strengthening oxidation system of the external micro-interfacial unit for producing PTA with PX, a volume of the third reaction zone accounts for 1.5% of the total reaction volume in the reactor.

Further, in the strengthening oxidation system of the external micro-interfacial unit for producing PTA with PX, the first micro-interfacial generator and the second micro-interfacial generator are both pneumatic micro-interfacial generators.

Compared with the prior art, the invention has the following beneficial effects: in the strengthening oxidation system of an external micro-interfacial unit for producing PTA with PX according to the invention, with the consideration of the rate difference of the four-step reaction of producing PTA with PX, a staged reaction concept is adopted, and the interior of the reactor is divided into three different reaction zones, each of which adopts different reaction steps, so that different conditions are given for different reaction stages in the same reactor, and particularly the contradiction that the acetic acid solvent may not withstand oxidation conditions of high temperature is solved. The water is used as the solvent for the p-TA oxidation reaction, which effectively solves the problem that the reaction solvent acetic acid is wasted in large quantities under high temperature and high pressure and the product TA may be taken out in time at the same time in the process of producing PTA with PX, thereby further greatly reducing energy consumption, saving acetic acid solvent and improving reaction efficiency.

In particular, in the strengthening oxidation system of an external micro-interfacial unit for producing PTA with PX according to the invention, through the disposition of the micro-interfacial generators in each of the reaction zones inside the reactor, the air is crushed into the micro bubbles with a diameter greater than or equal to 1 μm and less than 1 mm inside each of the reaction zones and the micro bubbles are mixed with the liquid phase material to form the emulsion, which effectively increases the mass transfer area between the air and the liquid material, reduces the thickness of the liquid film, and reduces the mass transfer resistance, thereby further effectively reducing the energy consumption and improving the reaction efficiency.

Further, in the strengthening oxidation system of an external micro-interfacial unit for producing PTA with PX according to the invention, through the disposition of the circulating heat exchange device, the temperature in the reaction process is effectively controlled, while ensuring the uniformity of mixing among the reaction materials inside the reactor and ensuring that the reaction materials may fully participate in the reaction, which further greatly improves the utilization rate of reactants while preventing the occurrence of side reactions caused by the unevenness of local temperatures to improve the quality of the product to a certain extent.

BRIEF DESCRIPTION OF THE DRAWINGS

Upon reading the following detailed description of preferred embodiments, various advantages and benefits will be apparent to those of ordinary skill in the art. The drawings are for the purpose of explaining preferred embodiments only, and do not constitute improper limitations on the present invention. The same components are also denoted by the same reference numerals throughout the drawings. In the drawings:

FIG. 1 is a structural diagram of a strengthening oxidation system of an external micro-interface unit for producing PTA with PX according to an embodiment of the present invention.

DESCRIPTION OF THE DRAWINGS

10—Outer casing;
11—Inner cylinder;
12—First reaction zone;
13—Second reaction zone;
14—Third reaction zone;
15—Anti-wave grille;
16—Defoamer net;
20—First circulating heat exchange pipeline;
21—Second circulating heat exchange pipeline;
30—First micro-interfacial generator;
31—Second micro-interfacial generator;
121—Heat exchange device;
122—Pressure pump.

DESCRIPTION OF THE PREFERRED EMBODIMENTS

The technical schemes of the present invention will be clearly and completely described below with reference to the accompanying drawings and specific embodiments, but those skilled in the art will understand that this embodiments described below are part of this embodiments of the present invention, rather than all of this embodiments. It is only used to illustrate the present invention and should not be construed as limiting the scope of the present invention. Based on this embodiments of the present invention, all other embodiments obtained by those of ordinary skill in the art without creative efforts shall fall within the protection scope of the present invention. It should be noted that, this embodiments of the present invention and the features of this embodiments may be combined with each other under the condition of no conflict. The present invention will be described in detail below with reference to the accompanying drawings and in conjunction with this embodiments.

With reference to FIG. 1, a strengthening oxidation system of an external micro-interfacial unit for producing PTA with PX is shown, which includes a reactor, a circulating heat exchange device and a micro-interfacial unit, wherein the reactor includes an outer casing 10 and an inner cylinder 11 disposed inside the outer casing 10. The inner cylinder 11 has a bottom end connected to an inner bottom surface of the outer casing 10 and a top end opened. A zone between the outer casing 10 and the inner cylinder 11 is a first reaction zone 12, and the first reaction zone 12 is a zone where p-xylene is converted into p-tolualdehyde and p-tolualdehyde is converted into p-toluic acid (i.e., the first two steps of oxidation reaction for producing PTA with PX). An interior of the inner cylinder 11 forms sequentially a second reaction zone 13 and a third reaction zone 14 from top to bottom. The second reaction zone 13 is a zone where the p-toluic acid is converted into 4-carboxy benzaldehyde (i.e., a $3^{rd}$ step of oxidation reaction for producing PTA with PX), and the third reaction zone 14 is a zone where the 4-carboxy benzaldehyde is converted into p-phthalic acid (i.e., a $4^{th}$ step of oxidation reaction for producing PTA with PX). Further, the outer casing 10 has a top end provided with an exhaust passage, and a top end provided with a gas phase inlet and a discharge port, wherein the gas phase inlet is connected with the external gas phase feed pipe for providing the gas phase material (an air) required for the reaction of the third reaction zone 14. The discharge port is used to take out a mixed material containing a reaction product, p-phthalic acid, in the third reaction zone 14. It can be understood that in the invention, with the consideration of the rate difference of the four-step reaction of producing PTA with PX, a staged reaction concept is adopted, and the interior of the reactor is divided into three different reaction zones, including the first reaction zone, the second reaction zone and the third reaction zone, each of which adopts different reaction steps, so that the purpose of providing different conditions for different reaction stages in the same reactor is achieved effectively, and particularly the contradiction that the acetic acid solvent may not withstand oxidation conditions of high temperature is solved. The water is used as the solvent for the p-TA oxidation reaction, which effectively solves the problem that the reaction solvent acetic acid is wasted in large quantities under high temperature and high pressure and the product TA may be taken out in time at the same time in the process of producing PTA with PX, thereby further greatly reducing energy consumption, saving acetic acid solvent and improving reaction efficiency.

In this embodiment, the reactor includes the outer casing 10 and the inner cylinder 11 disposed concentrically inside the outer casing 10, wherein the inner cylinder 11 has a bottom end being closed and connected to an inner bottom surface of the outer casing 10 and a top end that is opened and extends up to $4/5$ of a height of the outer casing 10 in an axial direction of the reactor. An annular zone between the outer casing 10 and the inner cylinder 11 is the first reaction zone 12 for performing the first two steps of oxidation reaction of producing PTA with PX, a volume of the first reaction zone accounts for 45% of a total reaction volume in the reactor, and an upper end of the zone is provided with a wave protection grille 15. The interior of the inner cylinder 11 forms sequentially the second reaction zone 13 for performing the third step of oxidation reaction of producing PTA with PX and a third reaction zone 14 for performing the fourth step of oxidation reaction of producing PTA with PX from top to bottom. A volume of the second reaction zone accounts for 53.5% of the total reaction volume in the reactor, a volume of the third reaction zone accounts for 1.5% of the total reaction volume in the reactor, and the wave protection grille 15 is disposed between the second reaction zone 13 and the third reaction zone 14. The outer casing 10 further has an upper portion provided with a defoamer net 16, a top portion provided with the exhaust passage, and a bottom portion provided with the gas phase inlet and the discharge port, wherein the gas phase inlet is connected with the external gas phase feed pipe for providing the gas phase material air required for the reaction of the third reaction zone. The discharge port is used to take out a mixed material containing a reaction product, p-phthalic acid, in the third reaction zone 14. It can be understood that in this embodiment, with the consideration of the rate difference of the four-step reaction of producing PTA with PX, a staged reaction concept is adopted, and the interior of the reactor is divided into three different reaction zones, each of which adopts different reaction steps, so that different conditions are given for different reaction stages in the same reactor, and particularly the reaction volume of each of the reaction zones is determined according to the reaction difficulty or reaction time of different reaction stages, which effectively ensures that all the reactions in the process of producing PTA with PX may be fully carried out, and further greatly improves the reaction efficiency of each of the reaction zones while solving the contradiction that the acetic acid solvent may not withstand oxidation conditions of high temperature, thereby finally effectively improving the yield of the product.

The circulating heat exchange device includes a first circulating heat exchange pipeline 20 and a second circulating heat exchange pipeline 21, wherein the first circulating heat exchange pipeline 20 is connected to an outside of the outer casing 10, and is connected with the micro-interfacial unit in series, for regulating a reaction temperature of the first two steps of oxidation reaction of producing PTA with PX (i.e., p-xylene is converted into p-tolualdehyde and p-tolualdehyde is converted into p-toluic acid) in the first reaction zone 12. The second circulating heat exchange pipeline 21 is disposed on the outside of the outer casing 10, and passes through the outer casing 10 to be connected with the inner cylinder 11 while being connected with the micro-interfacial unit in series, for regulating a reaction temperature of the last two steps of oxidation reaction of producing PTA with PX (i.e., the p-toluic acid is converted into 4-carboxy benzaldehyde and the 4-carboxy benzaldehyde is converted into p-phthalic acid) for the second reaction zone 13 and the third reaction zone 14 inside the inner cylinder 11. It can be understood that in this invention, through the disposition of the circulating heat exchange device, the reaction materials inside the reactor are continuously circulated in the reaction process, so that the reaction temperature in the reaction process is effectively controlled, and the problem that the solvent acetic acid is wasted in large quantities because of being not resistant to high temperature and high pressure is solved, while ensuring the uniformity of mixing among the reaction materials inside the reactor and effectively ensuring that the reaction materials may fully participate in the reaction, which further greatly improves the utilization rate of reactants while preventing the occurrence of side reactions caused by the unevenness of local temperatures to improve the quality of the product to a certain extent.

In this embodiment, the circulating heat exchange device includes the first circulating heat exchange pipeline 20 and the second circulating heat exchange pipeline 21, wherein the first circulating heat exchange pipeline 20 has an inlet end connected to an upper end of a side wall of the outer casing 10 and an outlet end connected with a material inlet of a bottom end of the side wall of the outer casing 10 through the micro-interfacial unit, for regulating the reaction temperature of the first two steps of oxidation reaction of producing PTA with PX in the first reaction zone 12. The second circulating heat exchange pipeline 21 has an inlet end connected to an upper end of a side wall of the inner cylinder 11 and an outlet end connected with a material inlet of a bottom end of the side wall of the inner cylinder 11 through the micro-interfacial unit, for regulating the reaction temperatures of the last two steps of oxidation reaction of producing PTA with PX in the second reaction zone 13 and the third reaction zone 14 inside the inner cylinder 11 in the reaction process. The first circulating heat exchange pipeline 20 and the second circulating heat exchange pipeline 21 are formed by connecting a heat exchanger 121 and a pressure pump 122 through pipes. It can be understood that in this embodiment, through the disposition of the first circulating heat exchange pipeline 20 and the second circulating heat exchange pipeline 21, the reaction materials of each of the reaction zones inside the reactor are continuously circulated in the reaction process respectively at the same time, so that the reaction temperature of each of the reaction zones in the reaction process is effectively controlled, and the problem that the solvent acetic acid is wasted in large quantities because of being not resistant to high temperature and high pressure in part of the reaction zones is solved, while ensuring the uniformity of mixing among the reaction materials in each of the reaction zones inside the reactor and effectively ensuring that the reaction materials in each of the reaction zones may fully participate in the reaction, which further greatly improves the utilization rate of reactants in each of the reaction zones while preventing the occurrence of side reactions caused by the unevenness of local temperatures in each of the reaction zones to greatly improve the quality of the product.

The micro-interfacial unit includes first micro-interfacial generators 30 and second micro-interfacial generators 31, wherein the first micro-interfacial generators 30 are connected in the first circulating heat exchange pipeline 20 in series, and are connected with the external feed pipe respectively, for crushing an air into micro bubbles with a diameter greater than or equal to 1 μm and less than 1 mm and mixing the micro bubbles with a liquid phase material to form an emulsion before a gas phase material air enters the first reaction zone 12, so as to perform the first two steps of reaction of producing PTA with PX in the first reaction zone, i.e., converting p-xylene into p-tolualdehyde and p-tolualdehyde into p-toluic acid, which effectively increases the mass transfer area between the air and the liquid phase material, reduces the thickness of the liquid film, and reduces the mass transfer resistance, thereby improving the reaction efficiency. The second micro-interfacial generators 31 are connected in the second circulating heat exchange pipeline 21 in series, and are connected with the feed pipe, for crushing the air into micro bubbles with a diameter greater than or equal to 1 μm and less than 1 mm and mixing the micro bubbles with the liquid phase material to form the emulsion before the gas phase material air enters the second reaction zone 13, so as to perform the third step of reaction of producing PTA with PX in the second reaction zone, i.e., converting the p-toluic acid into 4-carboxy benzaldehyde, which effectively increases the mass transfer area between the air and the liquid phase material, reduces the thickness of the liquid film, and reduces the mass transfer resistance, thereby improving the reaction efficiency. The specific structure of the micro-interfacial generator is reflected in the prior patents of the present inventor, such as the patent of publication number CN106215730A, the core of the micro-interfacial generator is bubble breaking, which will not be repeated here. The reaction mechanism and control method of the micro-interfacial generator have been disclosed in the inventor's prior patent CN107563051B, which will not be repeated here. It can be understood that in the invention, through the disposition of the micro-interfacial generators in each of the reaction zones inside the reactor, the air is crushed into the micro bubbles with a diameter greater than or equal to 1 μm and less than 1 mm inside each of the reaction zones and the micro bubbles are mixed with the liquid phase material to form the emulsion, which effectively increases the mass transfer area between the air and the liquid material, reduces the thickness of the liquid film, and reduces the mass transfer resistance, thereby further effectively reducing the energy consumption and improving the reaction efficiency.

In this embodiment, the micro-interfacial unit includes first micro-interfacial generators 30 and second micro-interfacial generators 31, wherein the first micro-interfacial generators 30 are disposed between the first circulating heat exchange pipeline 20 and the side wall of the outer casing 10, and are connected with the liquid phase material feed pipe 40 and the gas phase feed pipe 41 in the external feed pipe respectively, for crushing an air into micro bubbles with a diameter greater than or equal to 1 μm and less than 1 mm at the outside of the reactor and mixing the micro bubbles with a liquid phase material to form an emulsion before a gas phase material air enters the first reaction zone 12, so as to perform the first two steps of reaction of producing PTA with PX in the first reaction zone, i.e., converting p-xylene into p-tolualdehyde and p-tolualdehyde into p-toluic acid, which effectively increases the mass transfer area between the air and the liquid phase material, reduces the thickness of the liquid film, and reduces the mass transfer resistance, thereby improving the reaction efficiency. The second micro-interfacial generators 31 are disposed between the second circulating heat exchange pipeline 21 and the inner wall of the inner cylinder 11, and are connected with the gas phase feed pipe 41, for crushing the air into micro bubbles with a diameter greater than or equal to 1 μm and less than 1 mm and mixing the micro bubbles with the liquid phase material to form the emulsion before the gas phase material, the air, enters the second reaction zone 13, so as to perform the third step of reaction of producing PTA with PX in the second reaction zone 13, i.e., converting the p-toluic acid into 4-carboxy benzaldehyde, which effectively increases the mass transfer area between the air and the liquid phase material, reduces the thickness of the liquid film, and reduces the mass transfer resistance, thereby improving the reaction efficiency. It can be understood that in this embodiment, through the disposition of the micro-interfacial generators in each of the reaction zones inside the reactor, the air is crushed into the micro bubbles with a diameter greater than or equal to 1 μm and less than 1 mm inside each of the reaction zones and the micro bubbles are mixed with the liquid phase material to form the emulsion, which effectively increases the mass transfer area between the air and the liquid material, reduces the thickness of the liquid film, and reduces the mass transfer resistance, thereby further effectively reducing the energy consumption and improving the reaction efficiency.

As shown in FIG. 1, a working process of the strengthening oxidation system of an external micro-interfacial unit for producing PTA with PX according to this embodiment is:

The reactants (PX, solvent, catalyst, etc.) and the air enter the first micro-interfacial generators 30 outside the reactor, wherein the air is crushed into the micro bubbles with a diameter greater than or equal to 1 μm and less than 1 mm to be mixed with the liquid phase material to form the emulsion, and then enter into the first reaction zone 12 between the outer casing 10 and the inner cylinder 11 of the reactor (the volume of this zone accounts for 45% of the total reaction volume in the reactor; the configuration is carried out because the time used in the first two steps of producing PTA with PX is about 45% of the total time of all four steps). In this zone 12, the first two steps of reaction is performed, i.e., converting p-xylene into p-tolualdehyde and p-tolualdehyde into p-toluic acid, and in this zone 12, the temperature is controlled by the first circulating heat exchange pipeline 20, and the circulating materials are mixed with the air and the reaction raw materials in the first micro-interfacial generators 30 and return to the first reaction zone 12 again. As the reaction proceeds, the liquid level in the first reaction zone 12 gradually rises, overflows the inner cylinder 11 of the reactor, and enters the second reaction zone 13. In this zone 13, the $3^{rd}$ step of reaction is performed (the volume of this zone 13 accounts for 53.5% of the total reaction volume in the reactor), i.e., converting the p-toluic acid into 4-carboxy benzaldehyde. In this zone 13, the materials are heated through the second circulating heat exchange pipeline 21, and the circulating materials are fully mixed with the air through the second micro-interfacial generators 31 and then return to the second reaction zone 13. Subsequently, the products in the second reaction zone 13 enters the third reaction zone 14 through the wave protection grille 15 (the volume of this zone accounts for 1.5% of the total reaction volume in the reactor), forming a push flow to perform the fourth step of reaction, i.e., converting the 4-carboxy benzaldehyde is converted into p-phthalic acid. The air enters the third reaction zone 14 through the gas phase inlet at the lower end of the reactor to participate in the oxidation reaction. The reaction products are discharged from the outlet at the lower end of the reactor and enter a post-processing separation unit. The exhaust gas in the reactor passes through the defoamer net 16 at the upper end of the reactor and is discharged from the exhaust passage above the reactor, and then enters the exhaust post-processing section.

Obviously, it can be concluded that in the strengthening oxidation system of an external micro-interfacial unit for producing PTA with PX according to the invention, with the consideration of the rate difference of the four-step reaction of producing PTA with PX, a staged reaction concept is adopted, and the interior of the reactor is divided into three different reaction zones, each of which adopts different reaction steps, so that different conditions are given for different reaction stages in the same reactor, and particularly the contradiction that the acetic acid solvent may not withstand oxidation conditions of high temperature is solved. The water is used as the solvent for the p-TA oxidation reaction, which effectively solves the problem that the reaction solvent acetic acid is wasted in large quantities under high temperature and high pressure and the product TA may be taken out in time at the same time in the process of producing PTA with PX, thereby further greatly reducing energy consumption, saving acetic acid solvent and improving reaction efficiency.

In particular, in the strengthening oxidation system of an external micro-interfacial unit for producing PTA with PX according to the invention, through the disposition of the micro-interfacial generators in each of the reaction zones inside the reactor, the air is crushed into the micro bubbles with a diameter greater than or equal to 1 μm and less than 1 mm inside each of the reaction zones and the micro bubbles are mixed with the liquid phase material to form the emulsion, which effectively increases the mass transfer area between the air and the liquid material, reduces the thickness of the liquid film, and reduces the mass transfer resistance, thereby further effectively reducing the energy consumption and improving the reaction efficiency.

Further, in the strengthening oxidation system of an external micro-interfacial unit for producing PTA with PX according to the invention, through the disposition of the circulating heat exchange device, the temperature in the reaction process is effectively controlled, while ensuring the uniformity of mixing among the reaction materials inside the reactor and ensuring that the reaction materials may fully participate in the reaction, which further greatly improves the utilization rate of reactants while preventing the occurrence of side reactions caused by the unevenness of local temperatures to improve the quality of the product to a certain extent.

Finally, it should be noted that the above embodiments are merely used to explain the technical schemes of the present invention, but not to limit them. Although the present invention has been described in detail with reference to the foregoing embodiments, those of ordinary skill in the art should understand that: the technical schemes described in the foregoing embodiments can still be modified, or some or all of the technical features thereof can be equivalently replaced. However, these modifications or replacements do not make the essence of the corresponding technical schemes deviate from the scope of technical schemes of this embodiments of the present invention.

What is claimed is:

1. A strengthening oxidation system of an external micro-interfacial unit for producing PTA with PX, comprising:
    a reactor, a circulating heat exchange device and a micro-interfacial unit;
    wherein the reactor comprises an outer casing and an inner cylinder disposed concentrically inside the outer casing, the inner cylinder has a bottom end being closed and connected to an inner bottom surface of the outer casing and a top end extending to a top surface of the reactor, a zone between an interior of the outer casing and an exterior of the inner cylinder is a first reaction zone, and an interior of the inner cylinder forms sequentially a second reaction zone and a third reaction zone from top to bottom;
    the circulating heat exchange device is disposed at an exterior of the reactor, and is connected with the outer casing and the inner cylinder respectively, for regulating reaction temperatures of the first reaction zone, the second reaction zone and the third reaction zone inside the reactor in a reaction process of producing PTA with PX;
    the micro-interfacial unit is connected between the reactor and the circulating heat exchange device, and connected with an external feed pipe of the reactor, for crushing a gas phase material into micro bubbles with a diameter greater than or equal to 1 μm and less than 1 mm and for mixing the micro bubbles with a liquid phase material to form an emulsion at the exterior of the reactor before a reaction material enters each of the reaction zones inside the reactor;
    the circulating heat exchange device comprises a first circulating heat exchange pipeline and a second circulating heat exchange pipeline; and wherein:
        the first circulating heat exchange pipeline has an inlet end connected to an upper end of a side wall of the outer casing and an outlet end connected with a material inlet of a bottom end of the side wall of the outer casing through the micro-interfacial unit, for regulating the reaction temperature of the first reaction zone; and
        the second circulating heat exchange pipeline has an inlet end connected to an upper end of a side wall of the inner cylinder and an outlet end connected with a material inlet of a bottom end of the side wall of the inner cylinder through the micro-interfacial unit, for regulating the reaction temperature of the second reaction zone and the reaction temperature of the third reaction zone inside the inner cylinder in the reaction process;
    the micro-interfacial unit comprises a first micro-interfacial generator and a second micro-interfacial generator; and wherein:
        the first micro-interfacial generator is disposed between the first circulating heat exchange pipeline and the side wall of the outer casing, and is connected with a liquid phase feed pipe and a gas phase feed pipe in the external feed pipe, for crushing an air into the micro bubbles and forming the emulsion with the liquid phase material before the gas phase material enters the first reaction zone; and the second micro-interfacial generator is disposed between the second circulating heat exchange pipeline and the side wall of the inner cylinder, and is connected with the gas phase feed pipe, for crushing the air of the gas phase material into the micro bubbles and forming the emulsion with the liquid phase material before the gas phase material air enters the second reaction zone;

the first reaction zone is a reaction zone where p-xylene is converted into p-tolualdehyde and p-tolualdehyde is converted into p-toluic acid, the second reaction zone is a reaction zone where the p-toluic acid is converted into 4-carboxy benzaldehyde, and the third reaction zone is a reaction zone where the 4-carboxy benzaldehyde is converted into p-phthalic acid.

2. The strengthening oxidation system of the external micro-interfacial unit for producing PTA with PX according to claim 1, wherein a bottom of the reactor is provided with a gas phase inlet and a discharge port; and wherein:

the gas phase inlet is connected with the external gas phase feed pipe for providing the air of the gas phase material required for the reaction of the third reaction zone;

the discharge port is used to take out a mixed material containing a reaction product, p-phthalic acid, in the third reaction zone.

3. The strengthening oxidation system of the external micro-interfacial unit for producing PTA with PX according to claim 1, wherein a height of the inner cylinder is $4/5$ of a height of the outer casing.

4. The strengthening oxidation system of the external micro-interfacial unit for producing PTA with PX according to claim 1, wherein a volume of the first reaction zone accounts for 45% of a total reaction volume in the reactor.

5. The strengthening oxidation system of the external micro-interfacial unit for producing PTA with PX according to claim 1, wherein a volume of the second reaction zone accounts for 53.5% of the total reaction volume in the reactor.

6. The strengthening oxidation system of the external micro-interfacial unit for producing PTA with PX according to claim 1, wherein a volume of the third reaction zone accounts for 1.5% of the total reaction volume in the reactor.

7. The strengthening oxidation system of the external micro-interfacial unit for producing PTA with PX according to claim 1, wherein the first micro-interfacial generator and the second micro-interfacial generator are both pneumatic micro-interfacial generators.

* * * * *